United States Patent [19]

Seale et al.

[11] 4,377,710
[45] Mar. 22, 1983

[54] QUATERNIZED EPICHLOROHYDRIN ADDUCTS OF PERFLUORO SUBSTITUTED ETHANOLS

[75] Inventors: Virgil L. Seale, Houston, Tex.; James R. Stanford, Duncan, Okla.; James E. Briscoe, Duncan, Okla.; Glenn S. Penny, Duncan, Okla.

[73] Assignee: Nalco Chemical Company, Oak Brook, Ill.

[21] Appl. No.: 355,503

[22] Filed: Mar. 8, 1982

[51] Int. Cl.³ .................... C07C 87/68; C07C 87/30
[52] U.S. Cl. .................... 564/281; 564/285; 564/286; 564/292; 564/294
[58] Field of Search .............. 564/281, 292, 285, 286, 564/294

[56] References Cited

U.S. PATENT DOCUMENTS

| | | | |
|---|---|---|---|
| 2,764,602 | 9/1956 | Ahlbrecht | 260/404.5 |
| 3,171,861 | 3/1965 | Ahlbrecht | 562/285 |
| 3,496,109 | 2/1970 | Walker et al. | 564/294 |
| 4,057,554 | 11/1977 | Redmore et al. | 564/294 |
| 4,208,466 | 6/1980 | Szur | 260/458 F |
| 4,209,456 | 6/1980 | Billensteim et al. | |

Primary Examiner—James H. Reamer
Attorney, Agent, or Firm—John G. Premo; Robert A. Miller

[57] ABSTRACT

A composition represented by the formula:

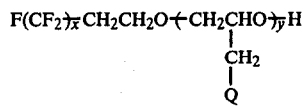

wherein x is an integer of from 2-12; y is an integer or fractional integer of from 1-20; Q is chosen from the group consisting of:
  (a) chloro, bromo, and iodo halogen radicals, and
  (b) a cationic nitrolgen radical represented by the formula:

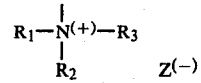

wherein $R_1$, $R_2$, and $R_3$ are aliphatic hydrocarbon radicals which contain from 1–30 carbon atoms and are further selected from the group consisting of alkyl, aryl, alkaryl and cyclo aliphatic radicals, with the proviso that when any of $R_1$, $R_2$, and $R_3$ exceed four carbon atoms, the other two hydrocarbon radicals are each chosen from the group consisting of ethyl and methyl hydrocarbon radicals; Z is a halogen anion chosen from the group consisting of chloride, bromide, and iodide with the further proviso that at least 50% of the radicals represented by Q are (b) radicals.

8 Claims, No Drawings

QUATERNIZED EPICHLOROHYDRIN ADDUCTS OF PERFLUORO SUBSTITUTED ETHANOLS

The perfluoro moiety is useful in the synthesis of surface active compounds and agents. However, the perfluoro moiety is characterized as being both lipophobic, as well as hydrophobic. The perfluoro moiety can be found in substances that are of anionic character such as is described in U.S. Pat. No. 4,208,466 and can also be found in fluorine containing alkyl-sulfatobetaines as described in U.S. Pat. No. 4,209,456. In addition, the last referenced U.S. patent also describes cationic compounds containing the perfluoro moiety attached to aromatic nitrogen containing functional groups which lead to a quaternary surface active compound containing both cationic charged nitrogen, as well as the perfluoro moiety.

The quaternized perfluorinated compounds are dispersible in water and, therefore, are more readily applicable in a number of end uses. Proposed starting materials for preparing quaternary perfluoro ammonia salts are the perfluoro substituted ethyl iodides represented by Formula I.

$$F(CF_2)_xCH_2CH_2I \qquad \text{Formula I}$$

where $x=2-12$

In the above Formula I, x is an integer ranging from 2-12 or an integer representing an average value of from 6-8. However, when these perfluoroalkyl iodides are reacted with strong basic amines such as trimethyl amines, no quaternary perfluoro salts are obtained. The lack of formation of the desired quaternary perfluoro salts is caused by a dehydrohalogenation reaction which occurs when these iodo-fluorocarbons are exposed to strongly basic reaction conditions. The result of this dehydrohalogenation reaction yields almost exclusively perfluoro olefin.

It would, therefore, be an advance in the art if one were able to obtain perfluoro quaternary salts using strong basic amine reactants without the disadvantages of strongly competing side reactions.

The present invention allows a variety of unique perfluoro quaternary amine salts to be prepared in good yield without olefin formation occurring and with excellent conversion of the expensive perfluoro precursor. The present invention further allows the balance of hydrophobicity and hydrophilicity by varying the ingredients and reactants used to prepare the finished compounds of the invention.

The present invention allows the synthesis of a variety of unique perfluoro quaternary amine compounds which have uses similar to those of commercial fluorocarbon surfactants. These compounds show utility in one or more of the following areas in which fluorocarbons are known to be effective:

(1) hydrocarbon emulsifiers in water;
(2) ore flotation aids;
(3) the treatment of porous substrates to modify surface characteristics (substrates such as leather, wood, porous plastics, and various natural or synthetic textiles may be treated);
(4) oil and water repellants;
(5) general surfactants;
(6) additives for dry powder fire extinguisher compositions;
(7) antimicrobials;
(8) soil repellants;
(9) additives for polishes and waxes;
(10) corrosion inhibitors for oils and lubricants;
(11) foaming and wetting agents;
(12) emulsifier and leveling agents for dye preparations.

THE INVENTION

The instant invention describes a perfluorohalogenated ether adduct (hereinafter the ADDUCT) which is easily quaternized by strong tertiary amines to yield very stable quaternized perfluoro compounds having exceptional surface active character. The compounds of the invention are represented by Formula II.

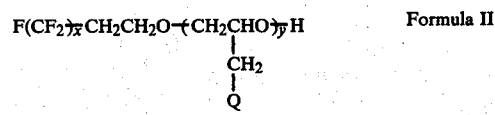

Formula II wherein x is an integer or fractional integer of from 2-12; y is an integer or fractional integer of from 1-20; Q is chosen from the group consisting of:
(a) chloro, bromo, and iodo halogen radicals, and
(b) a cationic nitrogen radical represented by the formula:

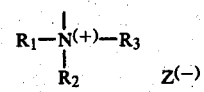

wherein $R_1$, $R_2$, and $R_3$ are aliphatic or aromatic hydrocarbon radicals which contain from 1-30 carbon atoms and are further selected from the group consisting of alkyl, aryl, alkaryl and cyclo aliphatic radicals, with the proviso that when any one of $R_1$, $R_2$, and $R_3$ exceed four carbon atoms, the other two hydrocarbon radicals are each chosen from the group consisting of ethyl and methyl hydrocarbon radicals; Z is a halogen anion chosen from the group consisting of chloride, bromide, and iodide with the further proviso that at least 50% of the radicals represented by Q are (b) radicals. Preferably between 80-100% of the radicals represented by Q are (b) radicals.

In the above formula, x is preferably an integer which has an average value between 6-8 and most preferably, an average value of 8. The term "average value" indicates that the formula may represent an admixture of compounds which contain molecules in which x may be any integer from 2-12. In the meaning of average value, x may be an integer, such as 8, or a fractional integer, such as 7.5, 7.8, 8.5, and the like. Also, in Formula II, y is preferably an integer or fractional integer between 1-4 and most preferably is an integer or fractional integer between 1.5-2.5.

Also, in Formula II, $R_1$, $R_2$, and $R_3$ are most preferably methyl radicals and Z preferably is the chloride anion. Q is preferably at least 80% trimethyl amine quaternary nitrogen radical with the remainder of Q being the chloro halogen radical. Q is most preferably exclusively represented by the trimethyl amine quaternary nitrogen radical.

The compositions represented above are obtained by following reaction conditions to be described later. The addition of less than equal molar quantities of cationizing amine gives partially quaternized or cationized product which also functions as an admixture surfactant in this invention.

The compositions of this invention are prepared by a reaction of a perfluoro alcohol with an epihalohydrin under anhydrous conditions. This reaction with the perfluoro alcohol is catalyzed by Lewis acid catalysts preferably chosen from the group consisting of antimony pentachloride, aluminum chloride, zinc chloride, ferrous or ferric chloride, boron trifluoride, and stannic chloride. Following the reaction of the perfluoro alcohol with epichlorohydrin to form the ADDUCT, the chloro group of the ADDUCT, which is originally found in the epihalohydrin molecule, is reacted with strong basic amines under controlled conditions, thereby obtaining the quaternized compounds of the instant invention.

The Starting Perfluoro Compounds

The starting perfluoro compounds which are used to generate perfluoronated substituents within the compositions of this invention are derived from perfluoro substituted ethanols which are represented by Formula III.

$F(CF_2)_xCH_2CH_2OH$            Formula III

In the above Formula III, x has the numerical values previously indicated in Formula II. A preferred perfluoro ethanol is commercially obtained from E. I. duPont de Nemours & Co. under the commercial name, "Zonyl BA." This material is generally described by Formula III, wherein x is equal to 6, 8, 10, 12 and wherein the average x is equal to 8. An average x, again, indicates that the compounds used may be an admixture of molecules wherein x is individually 6, 8, 10, 12 with the numerical average being about 8.

The Epihalohydrins

The starting epihalohydrins used to react with the perfluoronated alcohols previously described are chosen from the group consisting of epichlorohydrin, epibromohydrin, and epiiodohydrin. The preferred epihalohydrin is epichlorohydrin.

The Starting Amines

The starting amines used in the preparation of quaternary ammonium salts of the invention are lower aliphatic tertiary amines which contain from 1-30 carbon atoms per nitrogen substituted alkyl functional group. As an example, these amines may be trimethylamine, triethylamine, tripropylamine, or tributylamine. They may also be mixed tertiary amines such as diethylmonomethylamine, dimethylmonoethylamine, dimethylpropylamine, and the like. The steric hinderance effects exhibited by tributylamines and higher alkyl tertiary amines can prevent the successful quaternization of the ADDUCTS obtained when the perfluoronated alcohols previously described are reacted with eiphalohydrins. However, this steric effect may be minimized or totally eliminated if the tertiary amine used to obtain the desired quaternary ammonium salts of this invention contains at least one methyl radical substituent. Examples would include N-methyl, N-butyl, propyl amine, N,N-dimethlcoco amine and the like. Other amines which may be used to obtain the desired perfluoro quaternary ammonium salts of this invention would include any N,N-dimethyl substituted tertiary amine where the third hydrocarbon radical on the nitrogen may contain from 1 to 30 carbon atoms and which may be saturated or unsaturated alkyl, aryl, alkaryl, branched alkyl or alkaryl, or cyclic aliphatic hydrocarbon radicals.

An example of an aromatic substituted amine which may be successfully used in the invention would be N,N-dimethyl aniline. The most preferred amine used to prepare the quaternary ammonium salts of this invention is trimethyl amine.

The Catalysts

The catalysts used in the reaction between the perfluoro alcohols previously described and the epihalohydrins described above are chosen from Lewis acid materials. These catalysts are represented by antimony pentachloride, boron trichloride, boron trifluoride, stannic chloride, ferric and ferrous chloride, as well as the Lewis acid compounds previously mentioned. The Lewis acid preferred is antimony pentachloride used either as an etherate compound or as pure anhydrous material. The catalyst is used at a concentration ranging from 0.01% based on the final ADDUCT up to about 1.0% by weight based on the final ADDUCT weight. A preferred range of catalyst is between 0.1% and 0.5% by weight based on the final ADDUCT. A most preferred catalyst concentration, particularly in reference to the use of antimony pentachloride, is between 0.2 and 0.3% by weight of the final ADDUCT obtained in this reaction.

It has been found that basic catalysts, such as potassium hydroxide, sodium hydroxide and sodium methoxide do not yield the final ADDUCT of this instant invention when used to react the perfluoro alcohols described above with the epihalohydrins also previously mentioned.

Reaction Conditions, Synthesis of Perfluoro Quaternary Salts

The compounds of the invention are made using a two-step synthetic technique. The first reaction comprises the reaction of the perfluoroethanol material with the epihalohydrin under the catalytic conditions previously described. After this ADDUCT product is produced, it is then reacted with the tertiary amines described above to produce the finished quaternary perfluoro salts of this invention.

The reaction of the perfluoro alcohol with epihalohydrin is accomplished by using one of two methods set forth below. The description uses epichlorohydrin as the epihalohydrin.

Method 1: To an autoclave which has previously been charged with the perfluoro alcohol and catalyst, an amount of epichlorohydrin is added at such a rate so as to maintain a reaction temperature between 60° and 100° C. The reaction is catalyzed by a Lewis acid, preferably antimony pentachloride, and additional catalyst may be added simultaneously with the addition of epichlorohydrin. Epichlorohydrin may be used in higher molar quantities such that the molar ratio of perfluoro alcohol to epichlorohydrin will vary between 1:1 and 1:5 in the final ADDUCT. The preferred amount of epichlorohydrin is approximately 1.5 moles of epichlorohydrin charged to the autoclave per mole of perfluoro alcohol originally charged to the autoclave. The purpose of the 50% molar excess of epichlorohydrin is to obtain essentially complete reaction of the expensive perfluoro alcohol starting compounds. An equal molar ADDUCT may, however, be synthesized and is to be considered included in this teaching.

Once the epichlorohydrin is charged to the autoclave in its entirety, the autoclave is maintained at a temperature of at least 100° C. at the concurrent pressures which are normally obtained from the reactants and initial charging conditions for at least 30 minutes. The autoclave may be cooled and samples removed from the autoclave for analysis or further reaction. Additional epichlorohydrin may be charged to obtain higher mole ratios of epichlorohydrin and perfluoro alcohol.

Alternatively, the tertiary amine compound which is chosen to quaternize the formed ADDUCT may be added to the autoclave and the quaternization reaction commenced. All of the above reactions are anhydrous in nature and are accomplished in an inert atmosphere such as is obtained by a nitrogen environment. The quaternization reaction is not required to be anhydrous in nature. In fact, slight improvements in the product yields are obtained when water, methanol, ethanol, and other lower molecular weight alcohols, and mixtures of water with these lower molecular weight alcohols are present. The preferred method of quaternizing the ADDUCTS mentioned above include the addition of water, methanol, or mixtures thereof.

Method 2 uses a round-bottomed flask equipped with a condenser, stirrer, dropping funnel, and nitrogen bleed, to which is added the desired quantity of the perfluoro alcohol. The Lewis acid catalyst is added after nitrogen sparging of the perfluoro alcohol to achieve anhydrous conditions. The preferred catalyst is again antimony pentachloride. Epichlorohydrin is then added at such a rate to obtain and maintain a reaction temperature ranging between 60° and 100° C.

After addition of epichlorohydrin is complete, the reactants are heated for at least an additional 30 minutes at a temperature of about 100° C. As before, additional epichlorohydrin may be added so as to increase the mole ratio of the ADDUCT obtained. When the preferred ADDUCT is obtained, the quaternization reaction may be commenced in the same flask by adding the appropriate tertiary amine.

The reaction between the epichlorohydrin/perfluoro alcohol ADDUCT and the tertiary amine may be conducted using either one of two methods:

1. Quaternization Method—To the autoclave containing the perfluoro alcohol-epichlorohydrin ADDUCT (derived from Method 1 above) is added sufficient tertiary amine to react with the chloro functionality of the ADDUCT. Enough methanol may be added to the autoclave so as to dilute the reactants to approximately 50 weight percent. The reactants then are heated under pressure to temperatures not exceeding 120° C. until the quaternization reaction is essentially completed. The autoclave is cooled and the product is removed from the autoclave as the methanol solution. The product may be diluted to desired concentrations by either the addition of methanol or water.

2. Quaternization Method II—The perfluoro alcohol/epichlorohydrin ADDUCT generated from Method II above is added to a closed vessel along with sufficient tertiary amine to react with the chloro functionality of the epichlorohydrin ADDUCT. Sufficient methanol may be added to dilute the reactants to approximately 50 percent by weight. The closed vessel is heated in an oven to temperatures not exceeding 120° C. until quaternization is essentially completed. Again, concentrated solutions may be obtained by dissolving the product of these reactions in methanol or methanol-water solvent mixtures.

To better describe and exemplify the invention, the following examples are set forth:

EXAMPLE 1

Into a three-necked, round-bottomed flask equipped with stirrer, condensor, and pressure equalized addition funnel, was placed 232 grams (½ mole) of the duPont Zonyl BA perfluoro alcohol. A slow nitrogen purge created a nitrogen atmosphere within the flask which was maintained throughout the reaction. The flask contents were heated to 70° C. and 1 milliliter of $BF_3$ etherate was added. While stirring, 62 grams (approximately ⅔ moles) of epichlorohydrin was added to the flask in a drop-wise fashion. The reaction exotherm was kept below 95° C. by adjusting and controlling the addition rate of epichlorohydrin. The reaction mixture continued to exotherm throughout the addition of epichlorohydrin.

After epichlorohydrin addition was completed, the reactants were heated to approximately 110° C. and maintained at that temperature for approximately 1 hour. The flask contents were cooled to 70° C. and then the quaternization reaction was begun.

The quaternization reaction is obtained by transferring the flask contents to a pressure vessel and adding sufficient quantities of trimethylamine to quaternize all of the chloro groups contained in the synthesized epichlorohydrin perfluoro alcohol ADDUCT. An additional 10 grams of trimethylamine was added to the pressure flask to guarantee complete quaternization. During the quaternization step, the pressure flask was closed to the atmosphere, under pressure, and heated to temperatures of approximately 120° C. After quaternization was complete, the flask contents were cooled, the flask vented to the atmosphere, and the contents removed from the flask and diluted to desired concentrations by the addition of either methanol or water solvent.

EXAMPLE 2

Two hundred grams of a 1.5 mole ratio epichlorohydrin/perfluoro alcohol ADDUCT was charged to a PARR autoclave. The autoclave was heated to 120° C. and sufficient anhydrous trimethylamine was added to the autoclave to react with all the chlorine on the epichlorohydrin/perfluoro alcohol ADDUCT. Again, an excess of about 10 grams of trimethylamine was added to insure complete quaternization reaction.

Temperatures were maintained at 120° C. for two hours after all the trimethylamine had been added.

Upon cooling, the solid material which was the product of the reactions was removed from the autoclave and a small amount of water and methanol added to it to soften the material. The product was then dried and stripped of residual trimethylamine by heating this softened material in a flask while purging the flask with nitrogen. The dry product was then dissolved in a 2:1 methanol to water solvent mixture to obtain a 50% by weight concentrated solution.

EXAMPLE 3

To a PARR autoclave may be added 1 mole of duPont's Zonyl BA perfluoro alcohol. To this autoclave may also be added approximately 1 gram of anhydrous antimony pentachloride. The autoclave may then be closed and heated to approximately 60° C. with appropriate stirring.

At this point, 1.5 moles of epichlorohydrin may slowly be added to the autoclave. The addition will be controlled at a rate sufficient to maintain the exotherm from the reaction so that the autoclave contents do not exceed 100° C. After the epichlorohydrin is added, the autoclave is heated for at least an additional 30 minutes at temperatures between 100° C. and 120° C.

The autoclave is cooled to temperatures below 70° C. and 1.65 moles of triethylamine is added to the autoclave. In addition, sufficient methanol is added to the autoclave so that a 50 weight percent solution may be obtained after the quaternization reaction is complete. The autoclave is closed to the atmosphere and its contents are heated to temperatures approximately 100° C.-120° C. The quaternization reaction is completed within 2 hours, at which time the autoclave is cooled to ambient temperatures and the product removed. The invention may be diluted with additional methanol or water.

EXAMPLE 4

Four hundred twenty-eight grams of a Zonyl BA alcohol/1.5 moles epichlorohydrin ADDUCT is added to a pressure vessel along with 50 milliliters of a 50/50 volume mixture of water and methanol. Two hundred forty grams of N,N-dimethylcoco amine is then added to this mixture after the mixture has been heated to approximately 120° C. The reaction temperature is maintained at approximately 120° C. for a period of time sufficient to achieve the quaternization of the above-mentioned ADDUCT. It will be noted that the above-mentioned quaternization reaction yields an alkyl dimethyl amine quaternary product which still contained unreacted chloro groups derived from the original perfluoro alcohol/epichlorohydrin ADDUCT.

EXAMPLE 5

A mixture of 100 grams (0.1217 equivalence) of a Zonyl BA/1.5 epichlorohydrin ADDUCT and 14.8 grams (0.1217 moles) N,N-dimethylaniline were heated to 120° F. for a period of four hours. After cooling an equal weight of methanol (114.8 grams) was added to the reaction contents to give a 50 weight percent solution of quaternized ADDUCT. An analysis for chloride ion indicated that the quaternization reaction was essentially complete. The product was the N,N-dimethylanilinium chloride quaternary salt of the Zonyl BA/1.5 epichlorohydrin ADDUCT.

The following table lists the anticipated products which would be expected if the reactions outlined above were to be completed using the indicated reactants.

| FA/Epi ADDUCT | Amine Reactant | Anticipated Product |
| --- | --- | --- |
| 1:1.5 mole ratio | 1.5 moles TMA | FA/Epi/TMA, 1:1.5:1.5 |
| 1:1.5 mole ratio | 2.0 moles TMA | FA/Epi/TMA, 1:1.5:1.5 |
| 1:1.5 mole ratio | 1.0 moles TMA | FA/Epi/TMA, 1:1.5:1.0 |
| 1:3.0 mole ratio | 3.3 moles TMA | FA/Epi/TMA, 1:3.0:3.0 |
| 1:3.0 mole ratio | 3.3 moles TEA | FA/Epi/TEA, 1:3.0:3.0 |
| 1:3.0 mole ratio | 3.3 moles DMA | FA/Epi/DMA, 1:3.0:3.0 |
| 1:5.0 mole ratio | 5.5 moles TMA | FA/Epi/TMA, 1:5.0:5.0 |
| 1:2.0 mole ratio | 2.2 moles DMCHA | FA/Epi/DMCHA, 1:2:2.0 |
| 1:2.5 mole ratio | 2.75 moles TMA | FA/Epi/TMA, 1:2.5:2.5 |
| 1:2.5 mole ratio | 2.75 moles TEA | FA/Epi/TEA, 1:2.5:2.5 |
| 1:2.5 mole ratio | 2.75 moles DMIPA | FA/Epi/DMIPA, 1:2.5:2.5 |

FA = Fluoro alcohol, duPont Zonyl BA (or its equivalent)
Epi = Epichlorohydrin
DMA = N,N dimethyl aniline
TMA = Trimethyl amine
DMCHA = N,N dimethyl cyclohexylamine
TEA = Triethyl Amine
DMIPA = N,N dimethyl isopropylamine

Having thus described my invention, I claim:

1. A composition represented by the formula:

$$F(CF_2)_{\overline{x}}CH_2CH_2O(CH_2CHO)_{\overline{y}}H$$
$$|$$
$$CH_2$$
$$|$$
$$Q$$

wherein x is an integer of from 2-12; y is an integer or fractional integer of from 1-20; Q is chosen from the group consisting of:
(a) chloro, bromo, and iodo halogen radicals, and
(b) a cationic nitrogen radical represented by the formula:

$$R_1-\overset{|}{\underset{\underset{R_2}{|}}{N^{(+)}}}-R_3 \quad Z^{(-)}$$

wherein $R_1$, $R_2$, and $R_3$ are hydrocarbon radicals which contain from 1-30 carbon atoms and are further selected from the group consisting of alkyl, aryl, alkaryl and cyclo aliphatic radicals, with the proviso that when any of $R_1$, $R_2$, and $R_3$ exceed four carbon atoms, the other two hydrocarbon radicals are each chosen from the group consisting of ethyl and methyl hydrocarbon radicals; Z is a halogen anion chosen from the group consisting of chloride, bromide, and iodide with the further proviso that at least 50% of the radicals represented by Q are (b) radicals.

2. The composition of claim 1 where x has an average value of from 6-8; and $R_1$, $R_2$, and $R_3$ are each methyl radicals; and Z represents the chloride anion.

3. The composition of claim 1 where y has the value of 1.5 to 2.5.

4. The composition of claim 3 wherein Q is at least 80% trimethyl amine cationic nitrogen radical, the remainder of Q being represented by the chloro halogen radical.

5. The composition of claim 1 wherein x is an integer of from 2-12; y is an integer or fractional integer of from 1-20; Q is a cationic nitrogen radical represented by:

$$R_1-\overset{|}{\underset{\underset{R_2}{|}}{N^{(+)}}}-R_3 \quad Z^{(-)}$$

wherein $R_1$, $R_2$, and $R_3$ are aliphatic hydrocarbon radicals which contain from 1-30 carbon atoms and are further selected from the group consisting of alkyl, aryl, alkaryl, and cyclo aliphatic carbon radicals, with the proviso that when any of $R_1$, $R_2$, and $R_3$ exceed four carbon atoms, the other two hydrocarbon radicals are each chosen from the group consisting of ethyl and methyl hydrocarbon radicals; and Z is a halogen anion chosen from the group consisting of chloride, bromide, and iodide.

6. The composition of claim 5 wherein x has an average value of from 6-8; and $R_1$, $R_2$, and $R_3$ are each methyl radicals; and Z represents the chloride anion.

7. The composition of claim 6 wherein y has the value of 1.5 to 2.5.

8. The compositions of claims 1 and 5 wherein $R_1$ and $R_2$ are each chosen from the group consisting of methyl and ethyl hydrocarbon radical and $R_3$ is chosen from the group consisting of phenyl, cyclohexyl, and isopropyl hydrocarbon radicals.

* * * * *